United States Patent
Iwata

(10) Patent No.: US 8,357,911 B2
(45) Date of Patent: Jan. 22, 2013

(54) PARTICLE BEAM IRRADIATION SYSTEM AND PARTICLE BEAM THERAPY SYSTEM

(75) Inventor: Takaaki Iwata, Tokyo (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 243 days.

(21) Appl. No.: 12/866,169

(22) PCT Filed: Aug. 27, 2009

(86) PCT No.: PCT/JP2009/064969
§ 371 (c)(1),
(2), (4) Date: Aug. 4, 2010

(87) PCT Pub. No.: WO2011/024278
PCT Pub. Date: Mar. 3, 2011

(65) Prior Publication Data
US 2011/0147604 A1     Jun. 23, 2011

(51) Int. Cl.
*H01J 1/50* (2006.01)

(52) U.S. Cl. ......... 250/396 ML; 250/396 R; 250/492.1; 250/492.3

(58) Field of Classification Search .............. 250/396 R, 250/396 ML, 492.1, 492.3
See application file for complete search history.

(56) References Cited

U.S. PATENT DOCUMENTS

| | | | | |
|---|---|---|---|---|
| 6,936,832 B2 * | 8/2005 | Norimine et al. | ......... | 250/505.1 |
| 7,439,528 B2 * | 10/2008 | Nishiuchi et al. | ......... | 250/492.3 |
| 8,212,223 B2 * | 7/2012 | Iwata | ......... | 250/396 R |
| 2007/0000165 A1 | 1/2007 | Nyland | | |
| 2010/0207552 A1 * | 8/2010 | Balakin | ......... | 315/503 |

FOREIGN PATENT DOCUMENTS

| | | |
|---|---|---|
| JP | 06-068997 A | 3/1994 |
| JP | 2000-292600 A | 10/2000 |
| JP | 2005-296162 A | 10/2005 |
| JP | 2007-132902 A | 5/2007 |
| JP | 2007-525732 A | 9/2007 |
| JP | 2007-268035 A | 10/2007 |
| JP | 2008-272139 A | 11/2008 |
| JP | 2008-307206 A | 12/2008 |

OTHER PUBLICATIONS

International Search Report (PCT/ISA/210) issued on Sep. 16, 2009, by Japanese Patent Office as the International Searching Authority for International Application No. PCT/JP2009/064969.
First Office Action from the Japanese Patent Office for Japanese Application No. 2009-547880, dated Dec. 22, 2009 (English translation provided).

* cited by examiner

*Primary Examiner* — Michael Logie
(74) *Attorney, Agent, or Firm* — Buchanan Ingersoll & Rooney PC

(57) ABSTRACT

The objective is to eliminate the effect of the hysteresis of a scanning electromagnet so that there is obtained a particle beam irradiation system that realizes high-accuracy beam irradiation. There are provided a magnetic-field sensor that measures the magnetic field of a scanning electromagnet and an irradiation control apparatus that controls the scanning electromagnet based on a measurement magnetic field measured by the magnetic-field sensor and target irradiation position coordinates of a charged particle beam. The irradiation control apparatus is provided with an inverse map means that calculates a target magnetic field, based on the target irradiation position coordinates of the charged particle beam; and a compensator that outputs a control input, to the scanning electromagnet, for controlling the magnetic-field error between the target magnetic field and the measurement magnetic field to be the same as or smaller than a predetermined threshold value.

16 Claims, 4 Drawing Sheets

FIG. 3

| Bx \ By | $(B_0, B_1)$ | $(B_1, B_2)$ | ... | $(B_{m-1}, B_m)$ |
|---|---|---|---|---|
| $(B_0, B_1)$ | $S_{0,0}$ | $S_{0,1}$ | ... | $S_{0,m-1}$ |
| $(B_1, B_2)$ | $S_{1,0}$ | $S_{1,1}$ | | |
| ⋮ | ⋮ | | ⋱ | |
| $(B_{m-1}, B_m)$ | $S_{m-1,0}$ | | | $S_{m-1,m-1}$ | though actual irradiation, and by utilizing
PARTICLE BEAM IRRADIATION SYSTEM AND PARTICLE BEAM THERAPY SYSTEM

TECHNICAL FIELD

The present invention relates to a particle beam therapy system utilized in the medical field and R&Ds, and particularly to a particle beam irradiation system of a scanning type such as a spot-scanning type or a raster-scanning type and a particle beam therapy system.

BACKGROUND ART

In general, a particle beam therapy system is provided with a beam generation apparatus that generates a charged particle beam; an accelerator that is connected with the beam generation apparatus and accelerates a generated charged particle beam; a beam transport system that transports a charged particle beam that is accelerated by the accelerator so as to gain predetermined energy and then emitted; and a particle beam irradiation system, disposed at the downstream side of the beam transport system, for irradiating an irradiation subject with a charged particle beam. Particle beam irradiation systems are roughly divided into a broad irradiation method in which a charged particle beam is enlarged in a scattering manner by a scatterer, and the shape of the enlarged charged particle beam is made to coincide with the shape of an irradiation subject in order to form an irradiation field; and a scanning irradiation method (the spot-scanning method, the raster-scanning method, and the like) in which an irradiation field is formed by performing scanning with a thin, pencil-like beam in such a way that the scanning area coincides with the shape of an irradiation subject.

In the broad irradiation method, an irradiation field that coincides with the shape of a diseased site is formed by use of a collimator or a bolus. The broad irradiation method is a most universally utilized and superior irradiation method where an irradiation field that coincides with the shape of a diseased site is formed so as to prevent unnecessary irradiation onto a normal tissue. However, it is required to create a bolus for each patient or to change the shape of a collimator in accordance with a diseased site.

In contrast, the scanning irradiation method is a high-flexibility irradiation method where, for example, neither collimator nor bolus is required. However, because these components for preventing irradiation onto not a diseased site but a normal tissue are not utilized, there is required a beam emission accuracy that is higher than the beam emission accuracy of the broad irradiation method.

With regard to a particle beam therapy system, there have been implemented various inventions that raise the accuracies of an irradiation position and an irradiation dose. Patent Document 1 discloses an invention, stated below, that has an objective of providing a particle beam therapy system capable of accurately irradiating a diseased site. In the invention disclosed in Patent Document 1, there are stored, in a memory device, the amount of charged particle beams scanned by a scanning apparatus and the position of a charged particle beam detected by a beam position detector while the charged particle beam is emitted; then, by utilizing the stored scanning amount and the beam position, the scanning amount of the beam scanning apparatus is set by a control apparatus, in accordance with the beam position based on information about a treatment plan. The relationship, between the scanning amount and the beam position, that is obtained by actually performing irradiation is stored in the memory device; therefore, accurate irradiation of a diseased site can be expected.

Patent Document 2 discloses an invention, stated below, that has an objective of providing a particle beam therapy system capable of ensuring high safety and emitting a charged particle beam in a highly accurate manner. In the invention disclosed in Patent Document 2, a charged particle beam emitted from a charged particle beam generation apparatus is supplied to a scanning electromagnet that performs irradiation on an irradiation plane perpendicular to the traveling direction of the beam; then, the amount of charged particle beams emitted from the charged particle beam generation apparatus is controlled based on the position and the dose, on the irradiation plane, of the charged particle beam that passes through the scanning electromagnet. Specifically, the supply of a charged particle beam to the region, among a plurality of regions formed by dividing the irradiation plane, where a target dose has been achieved is stopped, and charged particle beams are supplied to the other regions where the target dose has not been achieved. As described above, the irradiation dose in each of the regions is compared with the target dose, and the emission amount of a charged particle beam is on/off-controlled (supplied/not stopped), so that high safety is expected.

Patent Document 3 discloses an invention, stated below, with regard to a problem that hysteresis characteristics existing in the relationship between the current and the magnetic field of a scanning electromagnet deteriorates the accuracy of a beam irradiation position. The invention disclosed in Patent Document 3 has a first calculation means that calculates, without taking the effect of the hysteresis into account, the current value of a scanning electromagnet in accordance with the beam irradiation position based on an irradiation plan; and a second calculation means that performs, taking the effect of the hysteresis into account, a correction calculation of the current value of the scanning electromagnet calculated by the first calculation means. An irradiation control apparatus controls the current of the scanning electromagnet, based on the result of the calculation by the second calculation means. As described above, a correction calculation is performed by the second calculation means so as to eliminate the effect of the hysteresis, i.e., the second calculation means has a mathematical model where the hysteresis characteristics are represented, so that the improvement of the accuracy of a beam irradiation position is expected through the calculation.

PRIOR ART REFERENCE

Patent Document

[Patent Document 1] Japanese Patent Application Laid-Open No. 2005-296162
[Patent Document 2] Japanese Patent Application Laid-Open No. 2008-272139
[Patent Document 3] Japanese Patent Application Laid-Open No. 2007-132902

DISCLOSURE OF THE INVENTION

Problems to be Solved by the Invention

In the invention disclosed in Patent Document 1, a transformation table is created based on actual data on the scanning amount and the position, of a charged particle beam, which are obtained through actual irradiation, and by utilizing this transformation table, the setting current value of a scanning electromagnet is calculated.

However, in fact, as disclosed in Patent Document 3, because there exist hysteresis characteristics between the current and the magnetic field of the scanning electromagnet, the magnetic field at a time when the current value increases differs from the magnetic field at a time when the current decreases. That is to say, even though the current value of the scanning electromagnet at an instant is obtained, the accurate value of the magnetic field cannot be determined only through the information. Accordingly, in the invention disclosed in Patent Document 1, there has been a problem that, due to the effect of the hysteresis of the electromagnet, accurate irradiation of a diseased site cannot be performed.

In the invention disclosed in Patent Document 2, the emission amount of a charged particle beam is on/off controlled (supplied/not supplied) in such a way that the irradiation dose at each of defined regions becomes a target dose.

However, the plurality of regions, formed on an irradiation plane through division, which are described in the invention disclosed in Patent Document 2 are regions (excitation regions) in the excitation current space defined by the range of the excitation current of the corresponding scanning electromagnet; thus, these regions do not coincide with regions (irradiation regions) in the actual irradiation space. That is because the excitation region and the irradiation region do not correspond to each other on a one-to-one basis unless the hysteresis of the scanning electromagnet is considered. Accordingly, even in an apparatus or a method where the irradiation dose for each excitation region is administered so as to raise the safety, there has been a problem that the accuracy of a beam irradiation position cannot be performed unless the effect of the hysteresis of the scanning electromagnet is eliminated.

In the invention disclosed in Patent Document 3, a mathematical hysteresis model is made in the inside of a calculation means, and through calculation, the current value of a scanning electromagnet is corrected.

However, even though the hysteresis is considered, there exist a number of problems. The first problem is that it is practically rather difficult to accurately correct the hysteresis characteristic by use of a calculation method. For example, the mode of the curve representing the hysteresis characteristic between the current and the magnetic field varies depending on not only the amplitude of the input (current) but also the speed of changing the input (current) or the changing pattern. In order to express the complicated hysteresis phenomenon by a calculation method, i.e., a mathematical model, studies and contrivances have been made for a long time in many fields; however, it is practically difficult to achieve it. The second problem is found in the method of detecting a beam irradiation position. As the invention disclosed in Patent Document 3, most of conventional methods try to detect a beam irradiation position by only a single beam position monitor or a plurality of beam position monitors. A beam position monitor does not learn a beam irradiation position by the time a charged particle beam is emitted. Accordingly, when a beam is way off the target and a normal tissue or the like is irradiated, all can be done is to stop the beam; thus, there has been a problem that the beam irradiation position cannot be controlled to fall on a right irradiation position onto which the beam should be emitted.

The present invention has been implemented in order to solve the foregoing problems; the objective thereof is to eliminate the effect of the hysteresis of a scanning electromagnet so that there is obtained a particle beam irradiation system that realizes high-accuracy beam irradiation.

Means for Solving the Problems

There are provided a magnetic-field sensor that measures the magnetic field of a scanning electromagnet; and an irradiation control apparatus that controls the scanning electromagnet, based on a measurement magnetic field measured by the magnetic-field sensor and the target irradiation position coordinates of a charged particle beam. The irradiation control apparatus is provided with an inverse map calculator that calculates a target magnetic field, based on the target irradiation position coordinates of a charged particle beam; and a compensator that outputs a control input, to the scanning electromagnet, for controlling the magnetic-field error between the target magnetic field and the measurement magnetic field to be the same as or smaller than a predetermined threshold value.

Advantage of the Invention

In a particle beam irradiation system according to the present invention, the effect of the hysteresis of a scanning electromagnet is eliminated, so that high-accuracy beam irradiation can be realized.

BRIEF DESCRIPTION OF THE DRAWINGS

FIG. 3 is a table representing a plurality of regions defined in a magnetic-field space.

BEST MODE FOR CARRYING OUT THE INVENTION

Embodiment 1

Figure 1:
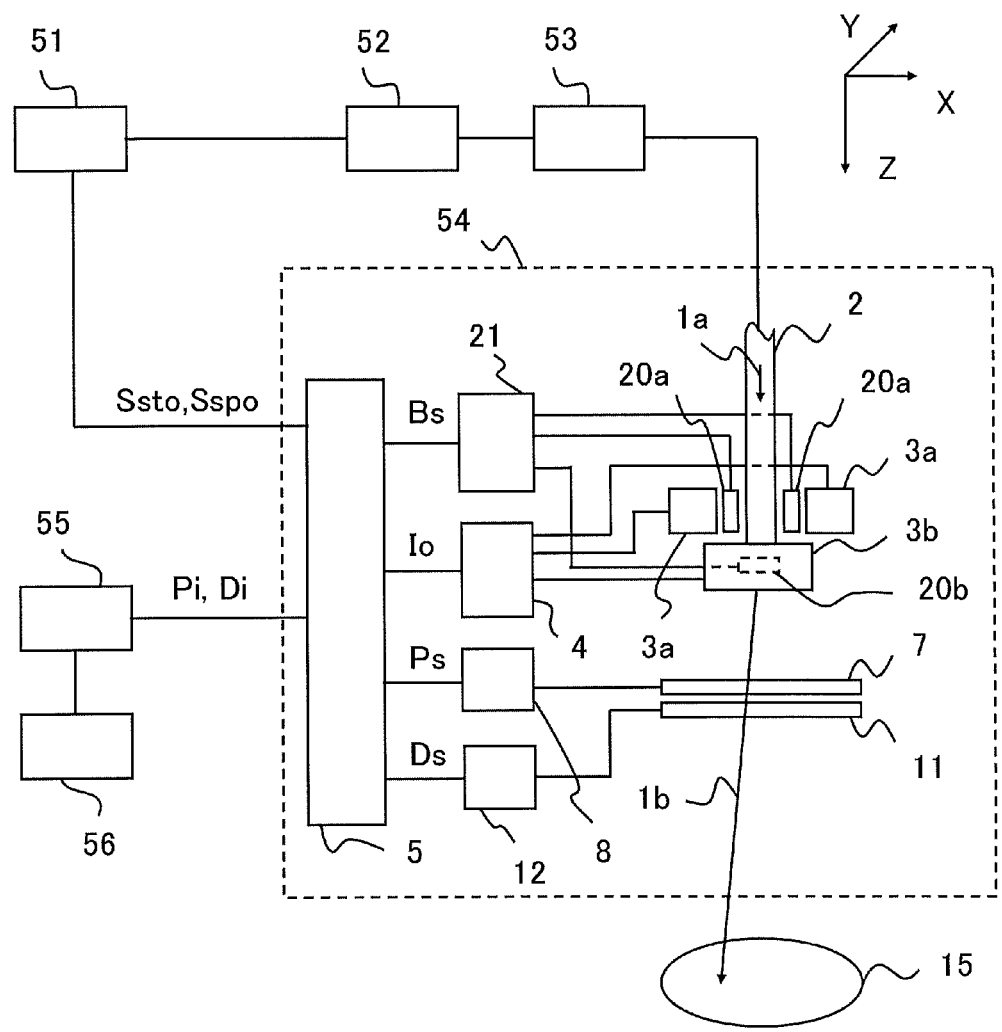
FIG. 1 is a schematic block diagram illustrating a particle beam therapy system according to Embodiment 1 of the present invention.

FIG. 1 is a schematic block diagram illustrating a particle beam therapy system according to Embodiment 1 of the present invention. The particle beam therapy system includes a beam generation apparatus 51, an accelerator 52, a beam transport apparatus 53, a particle beam irradiation system 54, a treatment plan apparatus 55, and a data server 56. The beam generation apparatus 51 generates a charged particle beam by accelerating charged particles generated in an ion source. The accelerator 52 is connected with the beam generation apparatus 51 and accelerates a generated charged particle beam. The beam transport apparatus 53 transports a charged particle beam that is accelerated by the accelerator 52 so as to gain predetermined energy and then emitted. The particle beam irradiation system 54 is disposed at the downstream side of the beam transport system and irradiates an irradiation subject 15 with a charged particle beam. The treatment plan apparatus 55 creates target irradiation position coordinates Pi, a target dose Di, and the like, which are treatment plan data items for the irradiation subject 15 of a patient. The data server 56 stores treatment plan data that is created by the treatment plan apparatus 55 for each patient.

The particle beam irradiation system 54 is provided with a beam transport duct 2 for transporting an incident charged particle beam 1a injected by the beam transport apparatus 53; scanning electromagnets 3a and 3b that scan the incident charged particle beam 1a in the X direction and the Y direction, respectively, which are directions perpendicular to the incident charged particle beam 1a; magnetic-field sensors 20a and 20b that detect magnetic fields generated by the scanning electromagnets 3a and 3b; a magnetic-field data converter 21; a beam position monitor 7; a position data converter 8; a dose monitor 11; a dose data converter 12; an irradiation control apparatus 5; and a scanning power source 4. The magnetic-field sensors 20a and 20b are, for example, magnetic-field sensors having a pickup coil. As illustrated in FIG. 1, the traveling direction of the incident charged particle beam 1a is the Z direction.

The scanning electromagnet 3a is an X direction scanning electromagnet that performs X-direction scanning with the incident charged particle beam 1a; the scanning electromagnet 3b is a Y direction scanning electromagnet that performs Y-direction scanning with the incident charged particle beam 1a. The magnetic-field sensor 20a is an X direction magnetic-field sensor that detects an X direction magnetic field; the magnetic-field sensor 20b is a Y direction magnetic-field sensor that detects a Y direction magnetic field. The magnetic-field data converter 21 converts magnetic fields detected by the magnetic-field sensors 20a and 20b into digital data and generates a measurement magnetic field Bs. The beam position monitor 7 detects the passing position of an outgoing charged particle beam 1b that has been deflected by the scanning electromagnets 3a and 3b. The position data converter 8 converts the passing position detected by the beam position monitor 7 into digital data and generates measurement position coordinates Ps. The dose monitor 11 detects the dose of the outgoing charged particle beam 1b. The dose data converter 12 converts the dose detected by the dose monitor 11 into digital data and generates a measurement dose Ds.

The irradiation control apparatus 5 controls the irradiation position on the irradiation subject 15, based on the measurement magnetic field Bs; when the measurement dose Ds reaches a target dose Di, the irradiation control apparatus 5 outputs a beam stop command Sspo to the beam generation apparatus 51 so as to stop the generation of a charged particle beam. The scanning power source 4 outputs an excitation current for driving the scanning electromagnets 3a and 3b, based on a command current Io, which is outputted from the irradiation control apparatus 5 and is a control input to a scanning electromagnet 3.

Figure 2:
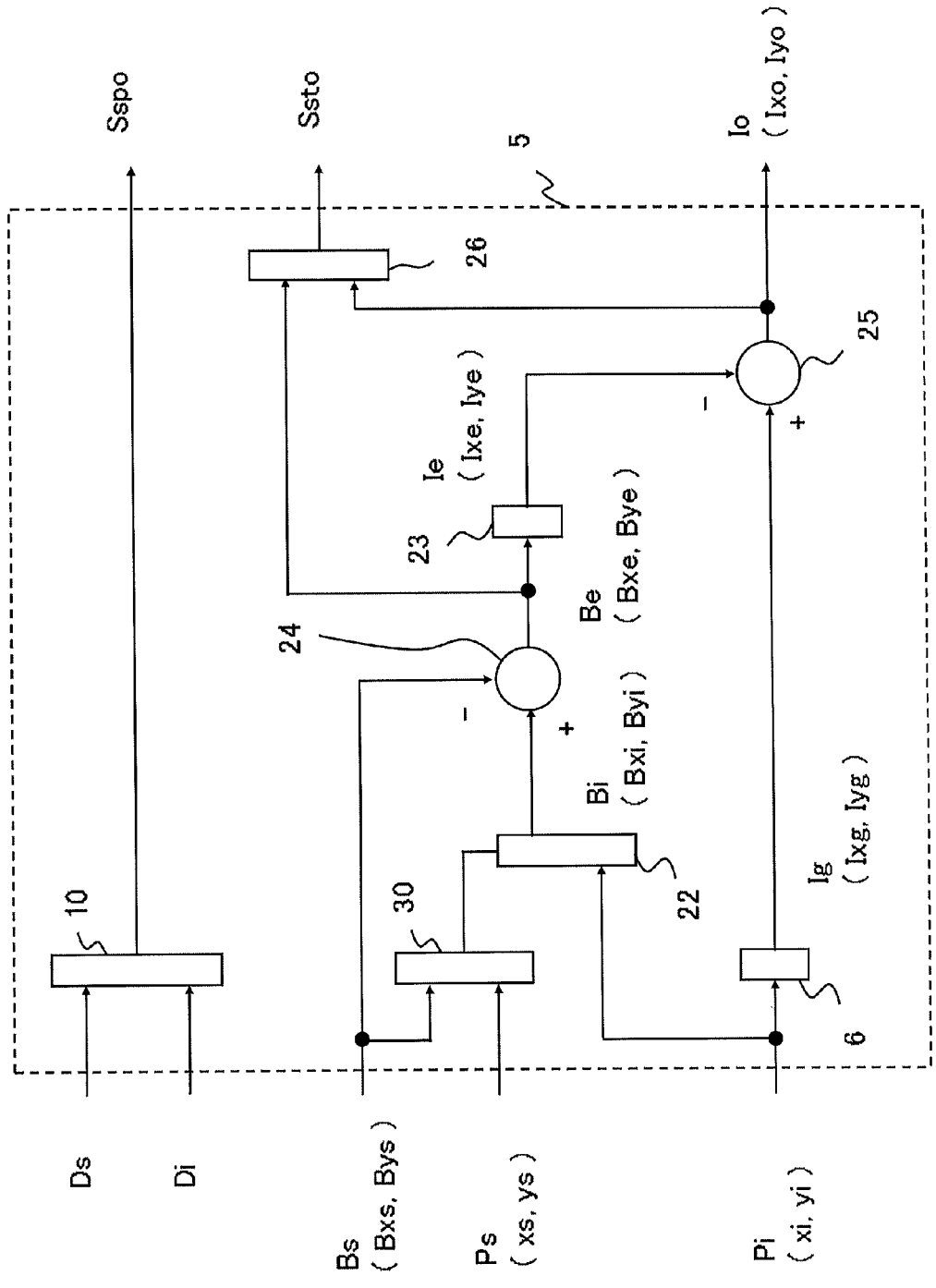
FIG. 2 is a block diagram of an irradiation control apparatus in FIG. 1.

FIG. 2 is a block diagram of an irradiation control apparatus 5. The irradiation control apparatus 5 has a scanning electromagnet command value generator 6, an inverse map generator 30, an inverse map calculator 22, an error calculator 24, a scanning electromagnet command value compensator 23, a command value outputting device 25, a beam supply starting command outputting device 26, and a dose administrator 10.

The operation of the irradiation control apparatus 5 will be explained. Irradiations by a particle beam therapy system are roughly divided into trial irradiation for calibration and proper irradiation for treatment. In general, trial irradiation for calibration is so-called irradiation for correction; trial irradiation for calibration is performed only when there exists no patient and correction is required. Each time trial irradiation is performed while varying a control input (current Ixo) to the X direction scanning electromagnet 3a and a control input (current Iyo) to the Y direction scanning electromagnet 3b, the irradiation position is measured. In Embodiment 1, trial irradiation for calibration is performed as is the case with a conventional irradiation control apparatus; however, when the trial irradiation is performed, not only the measurement position coordinates Ps (xs, ys) of a beam are measured, but also the measurement magnetic field Bs (Bxs, Bys) are measured by use of the magnetic-field sensors 20a and 20b. In this situation, the relationship between the measurement magnetic field Bs (Bxs, Bys) of the scanning electromagnet 3 and the measurement position coordinates Ps (xs, ys) of a beam is realized as a mathematical expression model, of the inverse map calculator 22, which is generated by the inverse map generator 30.

The data string of trial-irradiation target irradiation position coordinates Pi and the data string of target dose Di, which are created by the treatment plan apparatus 55, are transmitted to the irradiation control apparatus 5 of the particle beam irradiation system 54 (step S001). The trial-irradiation target irradiation position coordinates Pi are coordinates within the range that can be irradiated by the particle beam irradiation system 54; the trial-irradiation target dose Di is an arbitrary dose. The scanning electromagnet command value generator 6 generates a basic command current Ig (Ixg, Iyg) for each set of target irradiation position coordinates Pi (the step S002). The command value outputting device 25 outputs the basic command current Ig, as the command current Io (Ixo, Iyo), to the scanning power source 4. The scanning power source 4 controls the scanning electromagnet 3 in accordance with the command current Io (the step S003).

In response to an output signal suggesting that the command value outputting device 25 has outputted the command current Io, the beam supply starting command outputting device 26 outputs a beam supply command Ssto for making the beam generation apparatus 51 generate a beam. The beam generation apparatus 51 starts irradiation with a charged particle beam. The magnetic-field sensors 20a and 20b measure the magnetic field of the scanning electromagnet 3 controlled by the command current Io, and the measurement magnetic field Bs (Bxs, Bys) is inputted to the inverse map generator 30 by way of the magnetic-field data converter 21. The beam position monitor 7 measures the measurement position coordinates Ps (xs, ys) of the outgoing charged particle beam 1b with which scanning is performed by the scanning electromagnet 3, and the measurement position coordinates Ps is inputted to the inverse map generator 30 by way of the position data converter 8. The inverse map generator 30 stores the measurement magnetic field Bs (Bxs, Bys) and the measurement position coordinates Ps (xs, ys) in a memory, which is an incorporated storage device (the step S004).

The dose monitor 11 measures the measurement dose Ds of the outgoing charged particle beam 1b with which scanning is performed by the scanning electromagnet 3, and the measurement dose Ds is inputted to the dose administrator 10 by way of the dose data converter 12 (the step S005). The dose administrator 10 compares the target dose Di and the measurement dose Ds; when the measurement dose Ds exceeds the target dose Di, the dose administrator 10 outputs to the beam generation apparatus 51 the beam stop command Sspo for stopping the generation of a beam. In response to the beam stop command Sspo, the beam generation apparatus 51 stops the generation of the charged particle beam 1a. Next, the step S002 is resumed. Changing to the next target irradiation position coordinates Pi is performed; irradiation with a charged particle beam is started; then, the processing flow from the step S002 to the step S006 is repeated until the irradiation over the trial-irradiation irradiation subject range has been completed (the step S006).

The inverse map generator 30 creates a mathematical expression model, based on a series of the stored measurement magnetic field Bs (Bxs, Bys) and the stored measurement position coordinates Ps (xs, ys), and stores the created mathematical expression model in the inverse map calculator 22 (the step S007).

The mathematical expression model for the inverse map calculator 22 is realized, as a preferred example, by use of a polynomial expression. There will be explained the reason why the inverse map calculator 22 is adopted instead of a conventional transformation table. Under the assumption that the specification of the scanning electromagnet 3, the specification of the scanning power source 4, and the specifications of an irradiation beam (the irradiation energy, the incident beam position, and the like) are constant, if the magnetic field B (Bx, By) of the scanning electromagnet 3 is determined, the beam irradiation position coordinates P (x, y) is uniquely determined; thus, the physical phenomenon related to the relationship between the magnetic field B and the beam irradiation position coordinates P can be regarded as a positive map of two inputs and two outputs. However, in the case of proper irradiation for treatment, the target irradiation position coordinates Pi (xi, yi) of a beam is preliminarily given, and it is required to control the magnetic field B (Bx, By) of the scanning electromagnet 3 so as to realize the target irradiation position coordinates Pi (xi, yi) of the beam. In other words, in the case of proper irradiation for treatment, it is required to calculate the presumed values of the magnetic field B (Bx, By) of the scanning electromagnet 3, based on the target irradiation position coordinates Pi (xi, yi) of a beam, so as to realize the target irradiation position coordinates Pi (xi, yi) of the beam. Accordingly, in order to obtain the presumed values of the magnetic field B (Bx, By), the inverse map calculator 22 is required.

The outline of the method of realizing with a polynomial expression the mathematical expression model for the inverse map calculator 22 will be explained. Based on a plurality of beam measurement position coordinates Ps (xs, ys) and a plurality of measurement magnetic fields Bs (Bxs, Bys) measured during trial irradiation at a time when calibration is performed, there is obtained an inverse-map unknown parameter matrix Ac that satisfies the equation PscAc=Bsc. The matrix Psc is an irradiation position coordinate matrix obtained by arranging, in a row direction, a plurality of row elements calculated from the beam measurement position coordinates Ps (xs, ys), for example, six elements [1, xs, $xs^2$, ys, xsys, $ys^2$]; the matrix Bsc is a magnetic-field matrix obtained by arranging, in a row direction, a plurality of the measurement magnetic fields Bs (Bxs, Bys), as the row elements.

The inverse-map unknown parameter matrix Ac can be obtained by the following equation (1) represented through the least square method.

$$Ac = (Psc^T Psc)^{-1} Psc^T Bsc \quad (1)$$

where $Psc^T$ is a transposed matrix of the matrix Psc.

A target magnetic field Bi (Bxi, Byi), which is a magnetic field B necessary for realizing the target irradiation position coordinates Pi (xi, yi), can be obtained by the following equation (2), by use of the parameter matrix Ac obtained in such a way as described above.

$$Bi = PipAc \quad (2)$$

where Pip, which is a row element calculated from the beam target irradiation position coordinates (xi, yi), is an element applied for obtaining the parameter matrix Ac; in the foregoing case, Pip is a matrix [1, xi, $xi^2$, yi, xiyi, $yi^2$] having six elements.

In a conventional technology, there is created, as a transformation table, the relationship between the control inputs (current Ixo, current Iyo) to the scanning electromagnet 3 under calibration and the beam measurement position coordinates Ps (xs, ys); then, the transformation table is stored in the scanning electromagnet command value generator 6. The control input (current Ixo) to the X direction scanning electromagnet 3a and the control input (current Iyo) to the Y direction scanning electromagnet 3b are independently obtained from the x coordinate value (xi) of the beam target irradiation position coordinates Pi and from the y coordinate value (yi) of the beam target irradiation position coordinates Pi, respectively. However, in practice, the control input (current Ixo) to the X direction scanning electromagnet 3a affects both xi and yi of the beam target irradiation position coordinates Pi, and the control input (current Iyo) to the Y direction scanning electromagnet 3b also affects both xi and yi of the beam irradiation position, i.e., there exist interference terms; therefore, the method utilizing a transformation table, which is independently obtained, deteriorates the accuracy of an irradiation position.

In the particle beam irradiation system 54 according to Embodiment 1, there is realized, in the inverse map calculator 22, a mathematical expression model where Bxi and Byi of the target magnetic field Bi are represented by considering the interference terms between xi and yi of the target irradiation position coordinates Pi; therefore, unlike the conventional technology, the accuracy of the irradiation position of the outgoing charged particle beam 1b can be raised.

Next, there will be explained treatment proper irradiation in a particle beam therapy system according to Embodiment 1. Treatment proper irradiation is performed according to the following procedure.

For each irradiation subject 15, the data string of target irradiation position coordinates Pi and the data string of target doses Di, which are created by the treatment plan apparatus 55, are transmitted to the irradiation control apparatus 5 of the particle beam irradiation system 54 (step S101). The scanning electromagnet command value generator 6 generates a basic command current Ig (Ixg, Iyg) for each set of target irradiation position coordinates Pi (the step S102). The command value outputting device 25 outputs the basic command current Ig, as the command current Io (Ixo, Iyo), to the scanning power source 4. The scanning power source 4 controls the scanning electromagnet 3 in accordance with the command current Io (the step S103).

By use of a mathematical expression model, the inverse map calculator 22 calculates the target magnetic field Bi (Bxi, Byi), from target irradiation position coordinates Pi, with which a beam passes through the target irradiation position coordinates Pi, and outputs the target magnetic field Bi (Bxi, Byi) (the step S104).

The magnetic-field sensors 20a and 20b measure the magnetic field of the scanning electromagnet 3 controlled by the command current Io, and the measurement magnetic field Bs (Bxs, Bys) is inputted to the error calculator 24 by way of the magnetic-field data converter 21 (the step S105). The error calculator 24 calculates a magnetic-field error Be by comparing the target magnetic field Bi and the measurement magnetic field Bs (the step S106).

Based on the magnetic-field error Be outputted from the error calculator 24, the scanning electromagnet command value compensator 23 generates a current correction value Ie in the same manner as a PID compensator. For example, the scanning electromagnet command value compensator 23 generates the current correction value Ie according to the following equation (3) (the step S107).

$$Ie = KpBe \quad (3)$$

where Kp is a proportional gain.

The command value outputting device 25 outputs a command current (Ig-Ie) obtained by correcting the basic command currents Ig with the current correction value Ie, as the command current Io (Ixo, Iyo), to the scanning power source 4. The scanning power source 4 controls the scanning electromagnet 3 in accordance with the command current Io (the step S108). When the magnetic-field error Be outputted from the error calculator 24 becomes the same as or smaller than a predetermined value, the beam supply starting command outputting device 26 outputs the beam supply command Ssto for making the beam generation apparatus 51 generate a beam. The beam generation apparatus 51 starts irradiation with a charged particle beam (the step S109).

The dose monitor 11 measures the measurement dose Ds of the outgoing charged particle beam 1b with which scanning is performed by the scanning electromagnet 3, and the measurement dose Ds is inputted to the dose administrator 10 by way of the dose data converter 12 (the step S110). The dose administrator 10 compares the target dose Di and the measurement dose Ds; when the measurement dose Ds exceeds the target dose Di, the dose administrator 10 outputs to the beam generation apparatus 51 the beam stop command Sspo for stopping the generation of a beam. In response to the beam stop command Sspo, the beam generation apparatus 51 stops the generation of the charged particle beam 1a. Next, the step S102 is resumed. Changing to the next target irradiation position coordinates Pi is performed; irradiation with a charged particle beam is started; then, the processing flow from the step S102 to the step S111 is repeated until the irradiation over the irradiation subject range has been completed (the step S111).

The depth-direction (Z direction) position coordinates of the irradiation subject 15 is controlled by varying energy of the incident charged particle beam 1a. Treatment proper irradiation is completed when irradiation over all the irradiation subject range including the depth-direction (Z direction) position coordinates of the irradiation subject 15 ends.

The dose administration of a charged particle beam performed in the step S111 is carried out for each of a plurality of small regions defined in the magnetic-field space as represented in FIG. 3. FIG. 3 is a table representing a magnetic-field small region Si, j defined by the magnetic-field space (Bx, By). (B0, B1) in the left column of the table briefly represents that the X component Bx of the magnetic field B satisfies the relationship $B0 \leq Bx < B1$; similarly, (Bm−1, Bm) briefly represents that Bx satisfies the relationship $Bm-1 \leq Bx < Bm$. (B0, B1) in the top row of the table briefly represents that the Y component By of the magnetic field B satisfies the relationship $B0 \leq By < B1$; similarly, (Bm−1, Bm) briefly represents that By satisfies the relationship $Bm-1 \leq By < Bm$. The region S0, 0 is a region that satisfies the relationships $B0 \leq Bx < B1$ and $B0 \leq By < B1$; the region Sm−1, m−1 is a region that satisfies the relationships $Bm-1 \leq Bx < Bm$ and $Bm-1 \leq By < Bm$.

Because being defined by magnetic fields including a hysteresis that occurs between the current and the magnetic field of the scanning electromagnet 3, the region defined in a magnetic field space is not affected by the hysteresis of the scanning electromagnet 3; therefore, the relationship, between the magnetic field detected by the magnetic-field sensor 20 and the beam position detected by the beam position monitor 7, which is obtained by performing calibration irradiation with a charged particle beam coincides very well with the relationship between the magnetic field and the beam position in the case of proper irradiation where irradiation with a charged particle beam is performed in the same manner as the calibration irradiation. An actual irradiation space can be obtained through the outgoing position of a charged particle beam, the passing position in the beam position monitor 7, and the positional relationship between the particle beam irradiation system 54 and the irradiation subject 15; thus, a region in the actual irradiation space has a mapping relationship with a region defined in the magnetic field space, and this mapping relationship hardly changes even in the case of proper irradiation. Accordingly, because charged particle beam dose administration is performed in the step S111 for each of a plurality of magnetic-field small regions Si, j defined in the magnetic-field space, dose administration in the actual irradiation space of the irradiation subject 15 can accurately be performed.

In the particle beam irradiation system 54 according to Embodiment 1, the incident charged particle beam 1a is feedback-controlled, based on the magnetic field generated by the scanning electromagnet 3, i.e., by directly detecting a state where there is included a hysteresis that occurs between the current and the magnetic field of the scanning electromagnet 3; therefore, the effect of the hysteresis of the scanning electromagnet 3 is eliminated, so that high-accuracy beam irradiation can be realized. Moreover, the magnetic field of the scanning electromagnet 3 is adopted as physical quantity with which the control input (command current Io) to the scanning electromagnet 3 is corrected; thus, the irradiation position of the incident charged particle beam 1a can be controlled without supplying the incident charged particle beam 1a. Accordingly, after making the irradiation position coordinates of the incident charged particle beam 1a coincide with the target irradiation position coordinates Pi without supplying the incident charged particle beam 1a, a charged particle beam is supplied; therefore, the irradiation subject 15 can be irradiated with a high-accuracy high-safety particle beam.

In the particle beam irradiation system 54, a plurality of regions defined by magnetic fields is feedback-controlled through a magnetic field measured by the magnetic-field sensor 20, and dose administration is performed in the magnetic region; thus, unlike the case where it takes a long time to perform conventional feedback control through position coordinates measured by the dose monitor 11, feedback control can be performed at high speed. As a result, irradiation time for the whole irradiation subject 15 can be shortened.

In the particle beam irradiation system 54, as the magnetic-field sensor 20, a magnetic-field sensor having a pickup coil is adopted; therefore, even in the case where a steep change in the magnetic field occurs, the magnetic field of the scanning electromagnet 3 can accurately be measured. Accordingly, because feedback control can be performed accurately and rapidly by use of the measurement magnetic field Bs measured by the magnetic-field sensor 20, high-speed scanning of a charged particle beam can be performed. As a result, irradiation time for the whole irradiation subject 15 can be shortened.

Figure 4:
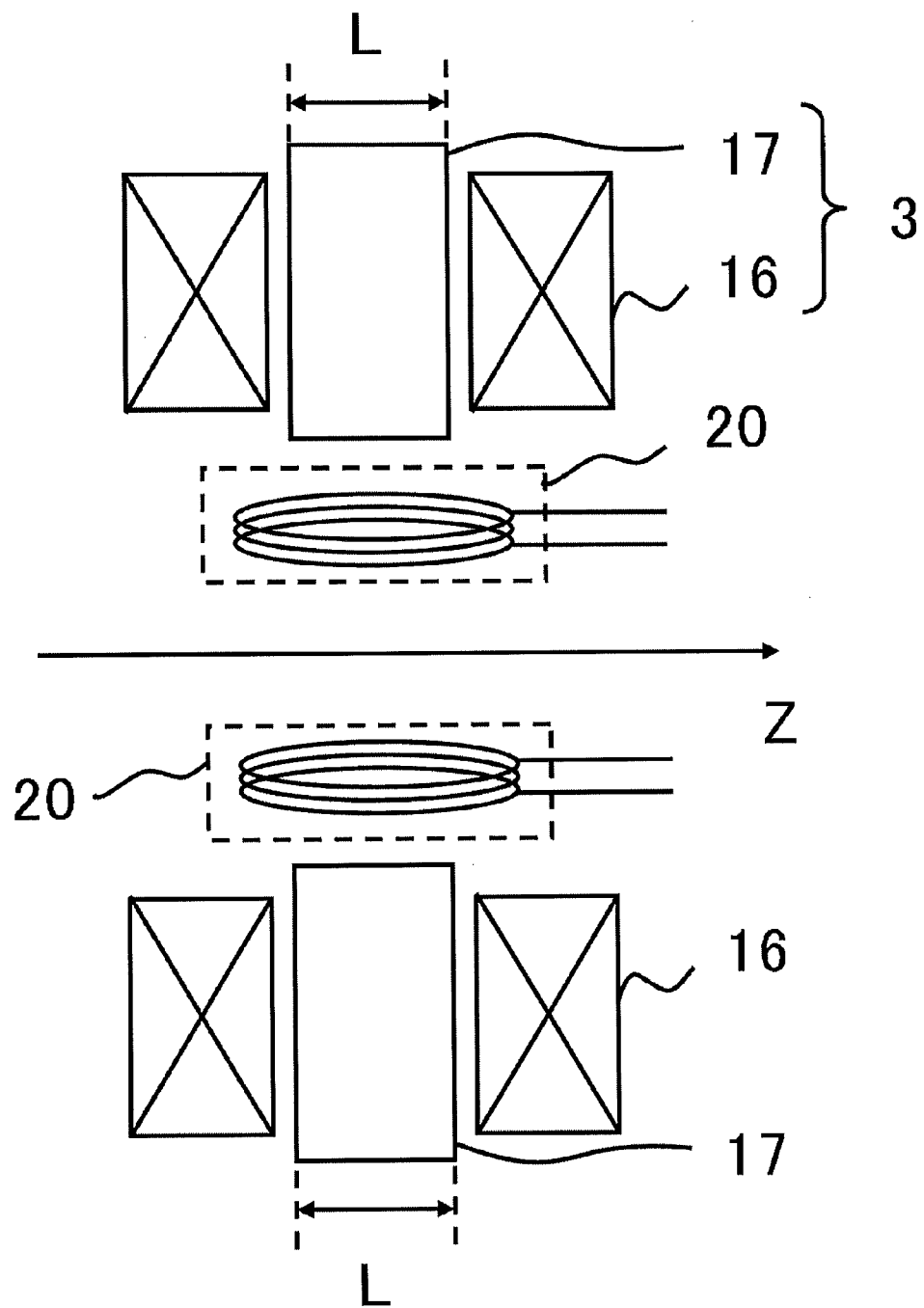
FIG. 4 is a view illustrating another magnetic-field sensor.

As the magnetic-field sensor 20, a magnetic-field sensor having a pickup coil illustrated in FIG. 4 may be adopted. FIG. 4 is a view illustrating another magnetic-field sensor 20; in the figure, the scanning electromagnet 3 and the magnetic-field sensor 20 are enlarged. The scanning electromagnet 3 has an iron core 17 and a winding 16. The magnetic-field sensor 20 illustrated in FIG. 4 is provided with a pickup coil having a length the same as or larger than the length L, of the iron core 17 of the scanning electromagnet 3, in the traveling direction (Z direction) of the charged particle beam 1a with which scanning has not been performed by the scanning electromagnet 3. Accordingly, there can be measured the spatial integration value, in the Z direction, of the magnetic field of the scanning electromagnet 3 that performs scanning with a charged particle beam. By utilizing the integration value of a magnetic field, the magnetic field that deflects a charged particle beam can accurately be measured; thus, feedback control of a charged particle beam can further accurately be performed. In addition, the X-direction magnetic-field sensor 20a and the Y-direction magnetic-field sensor 20b may be configured by arranging a plurality of magnetic-field sensors 20 in the Z direction.

In the case where scanning with a charged particle beam is performed slowly, the magnetic-field sensor 20 may be a magnetic-field sensor having a hall device. Because utilizing a hall device makes it possible to measure the absolute value of a magnetic field generated by the scanning electromagnet 3, it is not required to perform calculation, such as integration, of a voltage measured by a pickup coil. As a result, the magnetic-field data converter 21 can be simplified and downsized. In addition, the magnetic-field sensor 20 may be a magnetic-field sensor having both a pickup coil and a hall device. The initial value of the measurement magnetic field Bs is measured with a hall device, and a variation thereof is measured with the pickup coil, so that magnetic-field measurement can be performed at an arbitrary timing, whereby magnetic-field measurement time can be shortened. Accordingly, feedback control can be performed at high speed. As a result, irradiation time for the whole irradiation subject 15 can be shortened.

In a conventional particle beam irradiation system, a beam irradiation position has been detected only with a single beam position monitor or a plurality of beam position monitors, and a charged particle beam has been feedback-controlled based on measurement position coordinates. Arranging a great number of devices, such as a position monitor and the like, that cut off a charged particle beam leads to the enlargement of beam scattering; thus, there has been a problem that a desired beam spot diameter cannot be obtained.

In the particle beam irradiation system 54 according to Embodiment 1, when proper irradiation is performed, a charged particle beam is feedback-controlled based on a measurement magnetic field Bs measured by the magnetic-field sensor 20; therefore, the particle beam irradiation system 54 may be configured in such a way that in the case of proper irradiation, the beam position monitor 7 is moved by an unillustrated moving apparatus so that the outgoing charged particle beam 1b does not pass through the beam position monitor 7. The foregoing method can prevent the outgoing charged particle beam 1b from being scattered and enlarged by the beam position monitor 7. Accordingly, the beam spot diameter can be reduced. As a result, in the case where it is better to perform irradiation with a beam having a small diameter, treatment can be carried out with a suitable spot diameter.

As described above, in the particle beam irradiation system 54 according to Embodiment 1, there are provided the magnetic-field sensor 20 that measures the magnetic field of the scanning electromagnet 3 and the irradiation control apparatus that controls the scanning electromagnet 3 based on the measurement magnetic field Bs measured by the magnetic-field sensor 20 and the target irradiation position coordinates Pi of the charged particle beam 1b, and the irradiation control apparatus 5 is provided with the inverse map calculator 22 that calculates the target magnetic field Bi based on the target irradiation position coordinates Pi of the charged particle beam 1b and the compensator 23 that outputs the control input Io, to the scanning electromagnet 3, for controlling the magnetic-field error Be between the target magnetic field Bi and the measurement magnetic field Bs to be the same as or smaller than a predetermined threshold value; therefore, the effect of the hysteresis of a scanning electromagnet is eliminated, so that high-accuracy beam irradiation can be realized.

In a particle beam therapy system according to Embodiment 1, there are provided the beam generation apparatus 51 that generates a charged particle beam, the accelerator 52 that accelerates a charged particle beam generated by the beam generation apparatus 51, the beam transport apparatus 53 that transports a charged particle beam accelerated by the accelerator 52, and the particle beam irradiation system 54 that, by the scanning electromagnet 3, performs scanning with a charged particle beam transported by the beam transport apparatus 53 and emits the charged particle beam onto the irradiation subject 15; the particle beam irradiation system 54 is provided with the magnetic-field sensor 20 that measures the magnetic field of the scanning electromagnet 3 and the irradiation control apparatus that controls the scanning electromagnet 3 based on the measurement magnetic field Bs measured by the magnetic-field sensor 20 and the target irradiation position coordinates Pi of the charged particle beam 1b; and the irradiation control apparatus 5 is provided with the inverse map calculator 22 that calculates the target magnetic field Bi based on the target irradiation position coordinates Pi of the charged particle beam 1b and the compensator 23 that outputs the control input Io, to the scanning electromagnet 3, for controlling the magnetic-field error Be between the target magnetic field Bi and the measurement magnetic field Bs to be the same as or smaller than a predetermined threshold value. As a result, the effect of the hysteresis of a scanning electromagnet is eliminated, so that high-accuracy particle beam therapy can be realized through high-accuracy beam irradiation.

In addition, in Embodiment 1, as an example of scanning-type particle beam therapy system, a spot-scanning type has been explained; however, feedback control of a charged particle beam can also be applied to a raster-scanning type, because of the measurement magnetic field Bs measured by the magnetic-field sensor 20.

INDUSTRIAL APPLICABILITY

A particle beam irradiation system and a particle beam therapy system according to the present invention can preferably be applied to a particle beam therapy system utilized in the medical field and R&Ds.

DESCRIPTION OF REFERENCE NUMERALS

1a: incident charged particle beam
1b: outgoing charged particle beam
3: scanning electromagnet
3a: X direction scanning electromagnet
3b: Y direction scanning electromagnet
7: beam position monitor
11: dose monitor
15: irradiation subject
20: magnetic-field sensor
20a: magnetic-field sensor for X direction scanning electromagnet
20b: magnetic-field sensor for Y direction scanning electromagnet
22: inverse map calculator
23: scanning electromagnet command value compensator
30: inverse map generator
51: beam generation apparatus
52: accelerator
53: beam transport apparatus
54: particle beam irradiation system
Bi: target magnetic field
Bs: measurement magnetic field Pi: target irradiation position coordinates
Ps: measurement position coordinates
Di: target dose
Ds: measurement dose
Io: command current
Si, j: magnetic-field small region
Be: magnetic-field error

The invention claimed is:

1. A particle beam irradiation system comprising:
a scanning electromagnet that scans a charged particle beam accelerated by an accelerator and has a hysteresis;
a scanning power source that outputs an excitation current for driving the scanning electromagnet;
a magnetic-field sensor that measures a magnetic field of the scanning electromagnet driven by the excitation current; and
an irradiation control apparatus that controls the scanning power source, based on a measurement magnetic field measured by the magnetic-field sensor and target irradiation position coordinates of the charged particle beam, wherein the irradiation control apparatus is provided with an inverse map calculator that calculates a target magnetic field, based on the target irradiation position coordinates of the charged particle beam; and a controller that creates a command value for the excitation current, which is issued to the scanning power source, so as to make the magnetic-field error between the target magnetic field and the measurement magnetic field the same as or smaller than a predetermined threshold value, and that outputs the command value to the scanning power source.

2. The particle beam irradiation system according to claim 1, further including a dose monitor that measures a dose of the charged particle beam, wherein the irradiation control apparatus has a dose administrator that administrates an irradiation dose for each of small regions obtained by dividing the irradiation subject, based on a measurement dose measured by the dose monitor and a target dose.

3. The particle beam irradiation system according to claim 2, wherein the small regions administrated by the dose administrator are regions defined by an X direction magnetic field and a Y direction magnetic field that are measured by the magnetic-field sensor.

4. The particle beam irradiation system according to claim 3, wherein the inverse map calculator is formed of a polynomial expression including a plurality of the target irradiation position coordinates.

5. The particle beam irradiation system according to claim 3, further including a beam position monitor that measures the position of the charged particle beam, wherein the irradiation control apparatus has an inverse map generator that generates a mathematical expression model of the inverse map calculator, based on measurement position coordinates measured by the beam position monitor and a measurement magnetic field measured by the magnetic-field sensor.

6. The particle beam irradiation system according to claim 3, wherein the controller includes a PID compensator.

7. The particle beam irradiation system according to claim 2, wherein the inverse map calculator is formed of a polynomial expression including a plurality of the target irradiation position coordinates.

8. The particle beam irradiation system according to claim 2, further including a beam position monitor that measures the position of the charged particle beam, wherein the irradiation control apparatus has an inverse map generator that generates a mathematical expression model of the inverse map calculator, based on measurement position coordinates measured by the beam position monitor and a measurement magnetic field measured by the magnetic-field sensor.

9. The particle beam irradiation system according to claim 2, wherein the controller includes a PID compensator.

10. The particle beam irradiation system according to claim 1, wherein the magnetic-field sensor has a pickup coil.

11. The particle beam irradiation system according to claim 10, wherein the scanning electromagnet includes an iron core; and the pickup coil has a length larger than the length of the iron core of the scanning electromagnet in the traveling direction of the charged particle beam.

12. The particle beam irradiation system according to claim 1, wherein the inverse map calculator is formed of a polynomial expression including a plurality of the target irradiation position coordinates.

13. The particle beam irradiation system according to claim 1, further including a beam position monitor that measures the position of the charged particle beam, wherein the irradiation control apparatus has an inverse map generator that generates a mathematical expression model of the inverse map calculator, based on measurement position coordinates measured by the beam position monitor and a measurement magnetic field measured by the magnetic-field sensor.

14. The particle beam irradiation system according to claim 1, wherein the compensator controller includes a PID compensator.

15. A particle beam therapy system comprising:
a beam generation apparatus that generates a charged particle beam;
an accelerator that accelerates the charged particle beam generated by the beam generation apparatus;
a beam transport apparatus that transports a charged particle beam accelerated by the accelerator; and
a particle beam irradiation system that, by a scanning electromagnet, performs scanning with a charged particle beam transported by the beam transport apparatus and emits the charged particle beam onto an irradiation subject,
wherein the particle beam irradiation system is a particle beam irradiation system according to claim 1.

16. The particle beam irradiation system according to claim 1, wherein the irradiation control apparatus has a scanning electromagnet command value creator that creates a basic command value for the excitation current, based on the target irradiation position coordinates; and the controller creates a command value for the excitation current by correcting the basic command value.

* * * * *